(12) United States Patent
Asmus et al.

(10) Patent No.: US 9,962,461 B2
(45) Date of Patent: May 8, 2018

(54) CONFORMABLE COATING COMPOSITION

(71) Applicant: 3M INNOVATIVE PROPERTIES COMPANY, St. Paul, MN (US)

(72) Inventors: Robert A. Asmus, Hudson, WI (US); Hae-Seung Lee, Woodbury, MN (US); Dong-Wei Zhu, North Oaks, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 75 days.

(21) Appl. No.: 15/124,132

(22) PCT Filed: Mar. 2, 2015

(86) PCT No.: PCT/US2015/018261
§ 371 (c)(1),
(2) Date: Sep. 7, 2016

(87) PCT Pub. No.: WO2015/138175
PCT Pub. Date: Sep. 17, 2015

(65) Prior Publication Data
US 2017/0021052 A1    Jan. 26, 2017

Related U.S. Application Data

(60) Provisional application No. 61/950,284, filed on Mar. 10, 2014.

(51) Int. Cl.
| | |
|---|---|
| *A61L 26/00* | (2006.01) |
| *C09D 133/10* | (2006.01) |
| *C08F 230/08* | (2006.01) |
| *C09D 133/08* | (2006.01) |
| *C09D 143/04* | (2006.01) |
| *C09J 4/06* | (2006.01) |
| *C09J 133/08* | (2006.01) |
| *C09J 143/04* | (2006.01) |

(52) U.S. Cl.
CPC ........ *A61L 26/0014* (2013.01); *C08F 230/08* (2013.01); *C09D 133/08* (2013.01); *C09D 133/10* (2013.01); *C09D 143/04* (2013.01); *C09J 4/06* (2013.01); *C09J 133/08* (2013.01); *C09J 143/04* (2013.01)

(58) Field of Classification Search
None
See application file for complete search history.

(56) References Cited

U.S. PATENT DOCUMENTS

| | | | |
|---|---|---|---|
| 3,672,883 A * | 6/1972 | Frost | G03G 5/022 430/18 |
| 3,786,116 A | 1/1974 | Milkovich | |
| 3,836,377 A | 9/1974 | Delahunty | |
| 3,842,059 A | 10/1974 | Milkovich | |
| 4,182,823 A | 1/1980 | Schoenberg | |
| 4,565,883 A | 1/1986 | Sieger | |
| 4,650,826 A | 3/1987 | Waniczek | |
| 4,732,808 A | 3/1988 | Krampe | |
| 4,987,893 A | 1/1991 | Salamone | |
| 5,103,812 A | 4/1992 | Salamone | |
| 5,604,268 A | 2/1997 | Randen | |
| 5,981,621 A | 11/1999 | Clark | |
| 6,143,805 A | 11/2000 | Hickey | |
| 6,183,593 B1 | 2/2001 | Narang | |
| 7,008,680 B2 | 3/2006 | Everaerts | |
| 7,641,893 B2 | 1/2010 | Salamone | |
| 7,939,611 B2 * | 5/2011 | Brandom | A61B 17/12036 526/256 |
| 8,142,765 B2 | 3/2012 | Ferrari | |
| 2004/0138338 A1 * | 7/2004 | Wakabayashi | C09D 11/30 523/160 |
| 2005/0000642 A1 * | 1/2005 | Everaerts | C09J 7/22 156/273.1 |
| 2005/0142082 A1 | 6/2005 | Ferrari | |
| 2005/0175570 A1 | 8/2005 | Inoue | |
| 2007/0041935 A1 | 2/2007 | Salamone | |
| 2007/0054133 A1 | 3/2007 | Sherman | |
| 2007/0129474 A1 | 7/2007 | Salamone | |
| 2009/0068133 A1 * | 3/2009 | Mondet | A61K 8/8152 424/64 |
| 2010/0202992 A1 | 8/2010 | Mondet | |
| 2011/0166492 A1 | 7/2011 | Holm | |
| 2013/0224373 A1 | 8/2013 | Jariwalla | |
| 2014/0142269 A1 * | 5/2014 | Takemori | C08K 5/09 526/318.3 |
| 2015/0307668 A1 * | 10/2015 | Kalgutkar | C08F 220/18 528/26 |
| 2015/0322370 A1 * | 11/2015 | Matsui | C10M 145/14 508/463 |
| 2016/0303278 A1 * | 10/2016 | Stein | A61F 2/44 |
| 2017/0121576 A1 * | 5/2017 | Bartholomew | C09J 153/00 |
| 2017/0158796 A1 * | 6/2017 | Faul | C08F 255/026 |

FOREIGN PATENT DOCUMENTS

| | | | |
|---|---|---|---|
| WO | WO 2005-123011 | | 12/2005 |
| WO | WO 2012/091742 | * | 5/2012 |
| WO | WO 2013-049527 | | 4/2013 |
| WO | WO 2013-049543 | | 4/2013 |

OTHER PUBLICATIONS

Excerpt from Concise Polymeric Materials Encyclopedia, p. 542.*
Kawakami, "Silicone Macromers for Graft Polymer Synthesis", Polymer Journal, 1982, vol. 14, No. 11, pp. 913-917.
Kawakami, "Synthesis and Copolymerization of Polysiloxane Macromers", ACS Polymer Preprints, Apr. 1984, vol. 25, No. 1, pp. 245-247.
Kawakami, "Synthesis of silicone graft polymers and a study of their surface active properties", Macromolecular Chemistry and Physics, 1984, vol. 85, pp. 9-18.
Schultz, "Functionally Terminal Polymers via Anionic Methods", Anionic Polymerization, American Chemical Society, 1981, vol. 27, pp. 427-440.
International Search Report for PCT International Application No. PCT/US2015/018261, dated May 22, 2015, 3pgs.

* cited by examiner

*Primary Examiner* — Marc S Zimmer
(74) *Attorney, Agent, or Firm* — Kent S. Kokko

(57) ABSTRACT

A conformable coating composition comprising a crystalline copolymer, and use thereof in barrier coating is described.

14 Claims, No Drawings

CONFORMABLE COATING COMPOSITION

CROSS REFERENCE TO RELATED APPLICATIONS

This application is a national stage filing under 35 U.S.C. 371 of PCT/US2015/018261, filed Mar. 2, 2015, which claims the benefit of U.S. Application No. 61/950,284, filed Mar. 10, 2014, the disclosure of which is incorporated by reference in its/their entirety herein.

FIELD

The present disclosure relates to a conformable coating composition that comprises a crystalline copolymer and a solvent, and coatings therefrom that are useful as barrier films in medical applications.

BACKGROUND

Barrier products are used to protect the skin of patients who have incontinence, skin occlusion, frequent washes, ostomys, especially ileostomy and colostomies. The presence of high moisture and corrosive enzymes from body fluids can lead to devastating breakdown of the skin, which can then lead to fungal infection, denuding, and erosion of the skin.

Commonly used products for protecting skin are occlusive barrier pastes. These barrier pastes are messy to apply and clean up. Also, the pastes interfere with securing of ostomy devices.

Liquid, film-forming products have also been developed to be applied and to protect skin, such as disclosed in U.S. Pat. Nos. 5,103,812 and 4,987,893. To increase the durability liquid, film forming products, cyanoacrylates have been used such as disclosed in U.S. Pat. Nos. 6,183,593 and 6,143,805. Cyanoacrylates very quickly form a film over skin, and even over moist skin. Therefore, there is a risk of adhering two skin surfaces together. U.S. Pat. No. 7,641,893 discloses cyanoacrylates used in a conformable bandage and coating material for application to skin, and includes solvent to limit cyanoacrylate-containing surface from sticking together. However, even with these advances in cyanoacrylate-containing compositions for application to skin, cyanoacrylate containing coating are brittle and do not flex well on skin.

SUMMARY

The disclosed conformable coating provides a highly durable and resilient film useful for protecting and repairing surfaces such as skin and mucous membranes. The conformable coating composition comprises a crystalline copolymer, a solvent and an optional hemostatic agent such as a cyanoacrylate. In some embodiments the coating composition comprises an acrylate copolymer having at least 5% by wt. of a crystalline comonomer with a $T_m \geq 30°$ C. comprising interpolymerized monomer units of monomers having a pendent crystallizable group:

In one embodiment, the conformable coating composition comprises a crystalline copolymer and a solvent, which when dried provides a conformable coating. As used herein "crystalline copolymer" refers to a copolymer having a crystalline or crystallizable monomer units, as further described herein.

The coating composition, comprised of a volatile solvent and elastomer when formed as a coating are useful for protecting or treating skin, nails, tissues, organs and mucous membranes, e.g. bleeding injuries, surgical sites, skin ulcers, cuts, abrasions, incisions, cold sores, blisters, rashes, abraded gums and other oral surfaces, hemorrhoids and abraded body areas, and other mucosal membrane incisions and wounds. The coatings may also be used as surgical glues. A coating formed from the conformable coating composition comprises a solvent borne or dispersion of an elastomer.

"Alkyl" means a linear or branched, cyclic or acrylic, saturated monovalent hydrocarbon, e.g., methyl, ethyl, 1-propyl, 2-propyl, pentyl, dodecyl and the like.

"Alkylene" means a linear or a branched divalent saturated hydrocarbons, e.g., methylene, ethylene, propylene, 2-methylpropylene, pentylene, hexylene, dodecylene and the like.

"Alkenyl" means a linear or branched monovalent hydrocarbon unsaturated hydrocarbon having from three to about twelve carbon atoms.

"Aryl" means a monovalent aromatic, such as phenyl, naphthyl and the like.

"Arylene" means a polyvalent, aromatic, such as phenylene, naphthalene, and the like.

"Aralkylene" means a group defined above with an aryl group attached to the alkylene, e.g., benzyl, 1-naphthylethyl, and the like.

"Alkarylene means an aryl group as defined above with an alkyl group attached to an arylene;

As used herein, "(hetero)hydrocarbyl" is inclusive of hydrocarbyl alkyl and aryl groups, and heterohydrocarbyl heteroalkyl and heteroaryl groups, the later comprising one or more catenary (in-chain) heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

DETAILED DESCRIPTION

The conformable composition comprises a crystalline copolymer obtained from monomer(s) containing a crystalline monomer having a $T_m$ of $\geq 20°$ C., preferably $\geq 25°$ C., and comprises monomer units having crystallizable pendent groups "crystalline monomers", optional high $T_g$ monomers, optional silane functional monomers, and optional acid-functional monomers.

By "crystalline" it is meant that a monomer displays a crystalline melting point $\geq 30°$ C. when measured in the composition by differential scanning calorimetry (DSC) and the copolymer preferably has a $T_m$ of $\geq 20°$ C. The peak temperature of the observed endotherm is taken as the crystalline melting point. The crystalline phase includes multiple lattices in which the copolymer assumes a conformation in which there is a highly ordered registry in adjacent chemical moieties of the crystalline monomer. The packing arrangement (short order orientation) within the lattice is highly regular in both its chemical and geometric aspects. Generally, the monomer per se will have a $T_m > 30°$ C., however once incorporated into the copolymer, the $T_m$ may be depressed, yet the copolymer preferably exhibits a $T_m > 20°$ C.

It may be difficult to see low or weakly crystalline areas which may be present by DSC. The crystalline mp is also influenced by polymer drying conditions as well as post annealing. The alternating configuration of the monomer units along the polymer chain will also influence this. Short chain blocks of the crystalline monomer will improve the formation of crystalline units.

A crystalline monomer or copolymer may be in a "semicrystalline state" in that long segments of polymer chains (or the crystallizable pendent groups of the monomer units) appear in both amorphous and crystalline states or phases at 20° C. or above. The amorphous phase is considered to be a randomly tangled mass of polymer chains. The X-ray diffraction pattern of an amorphous polymer is a diffuse halo indicative of no ordering of the polymer structure. Amorphous polymers show softening behavior at the glass transition temperature, but no true melt or first order transition. A material in a semicrystalline state shows characteristic melting points, above which the crystalline lattices become disordered and rapidly lose their identity. The X-ray diffraction pattern of such "semicrystalline" materials generally is distinguished by either concentric rings or a symmetrical array of spots, which are indicative of the nature of the crystalline order. Thus, herein a "crystalline" component encompasses semicrystalline materials. The crystalline copolymer includes at least one monomer that crystallizes, exhibiting a $T_m > 30°$ C. Such crystallinity, that may be provided by the aggregation of crystallizable moieties present in the component (e.g., when the component is a polymer, in the backbone (i.e., main chain) or pendant substituents (i.e., side chains) of the component), can be determined by well known crystallographic, calorimetric, or dynamic/mechanical methods. For the purposes of the present invention, this monomer component preferably imparts to the copolymer at least one melting temperature ($T_m$) as measured experimentally (for example by DSC) of greater than about 30° C. Preferably, this component imparts a $T_m$ to the copolymer system of about 30-100° C. If more than one crystalline material is used in the crystalline component, more than one distinct melting point may be seen. Although the observation of a distinct melt point is preferable it is not necessarily required, as small amounts of crystalline reinforcement which are adequate to providing improved elongation of the polymer as well as reduced tack by increasing the modulus of the polymer may not be observeable due to the device's sensitivity, The copolymer comprises monomer units, $[M^{xstal}]$ having crystallizable pendent groups of the formula:

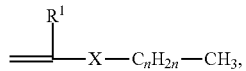

where
$R^1$ is hydrogen or a ($C_1$-$C_4$) alkyl group,
X is —$CH_2$—, —C(O)O—, —O—C(O)—, —C(O)—NH—, —HN—C(O)—, —O—, —NH—, O—C(O)—NH—, —HN—C(O)—O, —HN—C(O)—NH—, —SiO($CH_3$)$_2$—, or —Si($CH_3$)$_2$—, and n is great enough to provide sufficient side chain length and conformation to form polymers containing crystalline domains or regions.

The crystalline monomer preferably imparts at least one distinct crystalline melting point to the copolymer above 20° C. Generally n is ≥18.

In one embodiment, the crystallizable monomer may be selected from (meth)acrylate ester monomers of linear primary alkanols of at least 18 carbon atoms, preferably 20-30 carbon atoms. Preferably the crystallizable pendent alkyl has fewer than 40 carbon atoms.

In another embodiment, the crystallizable monomer may be selected from (meth)acrylate ester monomers of secondary alcohols or branched alkanols, having an linear, unbranched alkyl or alkylene segment of at least 18 carbon atoms.

In another embodiment, the crystallizable monomer may be selected from alkenyl esters, having an linear, unbranched, saturated alkyl or alkylene segment of at least 18 carbon atoms. Preferably the alkenyl esters are of at least 24 carbon atoms.

In another embodiment, the crystallizable monomer may be selected from aralkyl or aralkenyl esters having an linear, unbranched, saturated alkyl or alkylene segment of at least 18 carbon atoms. Preferably the aralkyl or aralkenyl esters have at least 24 carbon atoms.

In another embodiment the crystallizable monomer may be selected from crystalline macromers of (meth)acrylate ester monomers of at least 16 carbon atoms.

The crystalline macromers are polymeric materials having a polymerizable group. The macromer is represented by the general formula X—(Y)$_n$—Z wherein
X is a polymerizable vinyl or acrylate group;
Y is a divalent linking group where n can be zero or one; and
Z is a monovalent polymeric moiety having a $T_m$≥ than 30° C. and a weight average molecular weight in the range of about 2,000 to 30,000 and being essentially unreactive under copolymerization conditions.

The preferred macromer useful in the present invention may be further defined as having an X group which has the general formula

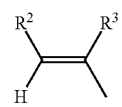

wherein $R^2$ is a hydrogen atom or a COOR$^3$ group and $R^3$ is a hydrogen atom or $C_1$-$C_4$ alkyl group.

The preferred C macromer useful in preparing compositions according to the present invention includes a Z group which has the general formula —(CH$_2$CH$_2$)$_m$—R$^3$ wherein m is an integer from 20 to 500 and R$^3$ is a lower alkyl group.

The crystalline macromer is a functionally terminated polymer having a single polymerizable functional group and is sometimes identified as a "semitelechelic" polymer. (Vol. 27 "Functionally Terminal Polymers via Anionic Methods" D. N. Schultz et al, pages 427-440, Anionic Polymerization, American Chemical Society [1981].) Such macromers are known and may be prepared by the method disclosed by Milkovich et al in U.S. Pat. Nos. 3,786,116 and 3,842,059, the disclosures of which are incorporated herein by reference for the description of the preparation of the vinyl-terminated macromers. As disclosed therein, vinyl-terminated macromer is prepared by anionic polymerization of a polymerizable monomer to form a living polymer. Such monomers include those having an olefinic group, such as the vinyl-containing compounds. Living polymers are conveniently prepared by contacting the monomer with an alkali metal hydrocarbon or alkoxide salt in the presence of an inert organic diluent which does not participate in or interfere with the polymerization process. Monomers which are susceptible to anionic polymerization are well known.

Preferred crystalline polymeric materials are acrylate or methacrylate polymers derived from acrylate or methacrylate esters of non-tertiary higher alkyl alcohols. The alkyl groups of these alcohols contain at least about 18, preferably about 24-36 carbon atoms. Thus, the preferred crystalline polymeric materials of the present invention include poly(dodecyl acrylate), poly(isotridecyl acrylate), poly(n-tetradecyl acrylate), poly(n-hexadecyl acrylate), poly(n-hexadecyl methacrylate), poly(n-octadecyl acrylate), poly(behenyl acrylate), poly(eicosanyl acrylate), and mixtures thereof. Of these, poly(n-octadecyl acrylate), poly(behenyl acrylate), and mixtures or copolymers thereof are preferred. As determined by DSC, poly(octadecyl acrylate) has a melting point in the range of about 42° C. to about 49° C. with an enthalpy of fusion of about 77 Joules/gram and poly(behenyl acrylate) has a melting point in the range of about 62° C. to about 72° C. and an enthalpy of fusion of about 105 Joules/gram. These crystalline polymers are particularly preferred due to their solubility in organic solvents near and above their respective melting temperatures. This facilitates formation of a continuous crystalline component distinct from the copolymer component.

Also preferred are side chain crystalline polymeric materials derived from higher a-olefin monomers, such as poly(1-decene), poly(1-dodecene), poly(1-tetradecene) and poly(1-hexadecene), and higher vinyl esters, such as vinyl tetradecanoate, vinyl hexadecanoate and vinyl octadecanoate.

The crystalline monomer may constitute 5-90 parts by weight of the monomer mixture use in preparation of the crystalline copolymer, relative to 100 parts total monomer. When a monomer mixture containing less than 5 wt % of a crystalline monomer is used, the resulting polymer has insufficient crystallinity. When the monomer mixture includes greater than 90 wt % crystalline monomer(s), the copolymer tends to be brittle. Consequently, depending on the use, the polymer used is preferably prepared from a monomer mixture containing an amorphous monomer in addition to the crystalline monomer. The crystalline monomer content of the monomer starting substance is 10-90 parts by weight and more preferably 30-80 parts by weight, relative to 100 parts by weight total monomer.

The crystalline copolymer optionally contains silane monomers [$M^{Silane}$] including those with the following formula:

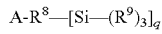

$$A\text{-}R^8\text{---}[Si\text{---}(R^9)_3]_q$$

wherein:
A is an ethylenically unsaturated polymerizable group, including vinyl, allyl, vinyloxy, allyloxy, and (meth)acryloyl, preferably (meth)acrylate;
$R^8$ is a covalent bond or a divalent (hetero)hydrocarbyl group, q is at least one, preferably greater than 1, more preferably 3;
$R^9$ is a monovalent alkyl, aryl or a trialkylsilyloxy group, q is 1, 2 or 3, preferably 1.

In one embodiment $R^8$ is a di- or polyvalent hydrocarbon bridging group of about 1 to 20 carbon atoms, including alkylene and arylene and combinations thereof, optionally including in the backbone 1 to 5 moieties selected from the group consisting of —O—, —C(O)—, —S—, —SO$_2$— and —NR$^1$— groups (and combinations thereof such as wherein $R^1$ is hydrogen, or a $C_1$-$C_4$ alkyl group. Preferably, $R^8$ is a divalent alkylene.

Useful silane monomers include, for example, 3-(methacryloyloxy) propyltrimethylsilane, 3-acryloxypropyltrimethylsilane, 3-acryloyloxypropyltriethylsilane, 3-(methacryloyloxy)propyltriethylsilane, 3-(methacryloyloxy) propylmethyldimethylsilane, 3-(acryloyloxypropyl) methyldimethylsilane, 3-(methacryloyloxy) propyldimethylethylsilane, 3-(methacryloyloxy) propyldiethylethylsilane, vinyldimethylethylsilane, vinylmethyldiethylsilane, vinyltriethylsilane, vinyltriisopropylsilane, vinyltrimethylsilane, vinyltriphenylsilane, vinyltri-t-butylsilane, vinyltris-isobutylsilane, vinyltriisopropenylsilane, vinyltris(2-methylethyl)silane, 3-(methacryloyloxy)propyl-tris-trimethylsilyl silane and mixtures thereof.

In other useful embodiments, the silane-functional monomer may be selected from silane functional macromers, such as those disclosed in US 2007/0054133 (Sherman et al.) and US 2013/0224373 (Jariwala et al.), incorporated herein by reference. The preparation of silane macromonomer and subsequent co-polymerization with vinyl monomer have been described in several papers by Y. Yamashita et al., Polymer J. 14, 913 (1982); ACS Polymer Preprints 25 (1), 245 (1984); Makromol. Chem. 185, 9 (1984), and in U.S. Pat. Nos. 3,786,116 and 3,842,059 (Milkovich et al.). This method of macromonomer preparation involves the anionic polymerization of hexamethylcyclotrisiloxane monomer to form living polymer of controlled molecular weight, and termination is achieved via chlorosilane compounds containing a polymerizable vinyl group. Free radical co-polymerization of the monofunctional siloxane macromonomer with vinyl monomer such as methyl methacrylate or styrene provides siloxane grafted co-polymer of well-defined structure, i.e., controlled length and number of grafted siloxane branches. Such macromers include poly(3-methacryloyloxypropyltris(trimethylsiloxy)silane (TRIS)-co-methyl methacrylate-co-isooctyl acrylate The optional silane monomers [$M^{Si}$] are used in amounts of 0 to 60, preferably 1-50, parts by weight, relative to 100 parts by weight total monomer. Such optional silane monomers are used promote solubility in siloxane solvents, but lower the $T_g$ of the resulting copolymer.

The polymer may further comprise an acid functional monomer [$M^{acid}$], where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

The presence of low amounts of acid functional monomers in the copolymer by enhancing the physical integrity and resilience by the ionic crosslinking (hydrogen bonding), and by stabilization of the cyanoacrylate due to the acidity of the carboxylic acid.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer, when present, is generally used in amounts of 0.1 to 10 parts by weight, preferably 0.5 to 5 parts by weight, based on 100 parts by weight total monomer of the copolymer.

In some embodiments the copolymer comprises a high monomer having a $T_g$ of at least 25° C., and preferably at least 50° C. [$M^{highTg}$]. In some instances, the copolymer is tacky and the addition of a high Tg monomer raises the $T_g$ and the modulus of the copolymer and reduces the tackiness. Suitable high $T_g$ monomers include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

Such high $T_g$ monomers are used in amounts sufficient to raise the $T_g$ of the copolymer to ≥0° C. Generally the high $T_g$ monomer, if present, is used in amounts of 5 to 50 parts by weight, relative to 100 parts of total monomer.

As long as a copolymer has a melting point, it can include noncrystallizable monomers. Acrylate or methacrylate or other vinyl monomers that are free-radically reactive may optionally be utilized in conjunction with one or more of the side chain crystallizable acrylate and methacrylate monomers provided that the resultant polymer has a melting or softening temperature above room temperature. Examples of such free-radically reactive monomers include, but are not limited to, tert-butyl acrylate, isobornyl acrylate, butyl methacrylate, vinyl acetate, acrylonitrile, styrene, isooctyl acrylate, n-butyl acrylate, 2-ethylhexyl acrylate, and the like. Various combinations of these monomers can be used. The amount and type is a function of the desired $T_m$ and $T_g$ of the copolymer.

Desirably, the $T_g$ of the copolymer is less than the $T_m$. A useful predictor of interpolymer $T_g$ for specific combinations of various monomers can be computed by application of Fox Equation: $1/T_g = \Sigma W_i/T_g i$. In this equation, $T_g$ is the glass transition temperature of the mixture, Wi is the weight fraction of component i in the mixture, and $T_g i$ is the glass transition temperature of component i, when polymerized as a homopolymer, and all glass transition temperatures are in Kelvin (K).

Preferably, the crystalline polymer component is not crosslinked, at least because preparation is easier, as crosslinked polymer tends to gel and provides high viscosity solutions which provide poor, non-uniform coatings which may suffer poorer elasticity.

The crystalline polymer to be used according to the invention may be synthesized by radical, anionic or cationic polymerization of the monomers comprising the crystalline monomer and the amorphous monomer, although synthesis by radical polymerization is preferred for ease of reaction with a greater variety of usable monomers. The initiator for the radical polymerization may be a thermal initiator which generates radicals by heat, or a photoinitiator which generates radicals by light.

Examples of thermal initiators which may be used include azo compounds such as 2,2'-azobis(2,4-dimethylvaleronitrile), 2,2'-azobisisobutyronitrile, 2,2'-azobis(2-methylbutyronitrile), 1,1'-azobis(1-cyclohexane-1-carbonylnitrile) and dimethyl-2,2'-azoisobutyrate, as well as peroxides such as benzoyl peroxide, lauroyl peroxide and t-butyl peroxypivalate. Examples of photoinitiators which may be used include benzoin ethers such as benzoin methyl ether and benzoin butyl ether, acetophenone derivatives such as 2,2-dimethoxy-2-phenylacetophenone and 2,2-diethoxyacetophenone, and acylphosphine oxide and acylphosphonate derivatives such as diphenyl-2,4,6-trimethylbenzoylphosphine oxide, isopropoxy(phenyl)-2,4,6-trimethylbenzoylphosphine oxide and dimethylpivaloylphosphonate.

A chain transfer agent may also be used during synthesis of the crystalline polymer to adjust the polymer molecular weight. Chain transfer agents which may be used are mercapto compounds such as dodecylmercaptan and halogen compounds such as carbon tetrabromide.

The resulting crystalline copolymer may be represented by the general formula: $\sim[M^{xstal}]_v\text{-}[M^{silane}]_w\text{-}[M^{acid}]_x\text{-}[M^{highTg}]\text{-}[M^{xlink}]_z$, which may be random or block and each subscript represents the parts by weigh to the monomer units.

The weight average molecular weight of the crystalline copolymer is generally 30,000-5,000,000. The weight average molecular weight of the crystalline polymer is preferably greater than 50,000 and up to 1,000,000, more preferably greater than 75,000 and up to 500,000.

The coating composition further comprises a volatile solvent. The composition has a viscosity less than 1,000 cps and a solubility parameter from 4.9-12.5 $(\text{cal/cm})^{1/2}$. In one embodiment, the volatile solvent is selected from the group consisting of volatile linear and cyclic siloxanes, volatile polydimethylsiloxanes, isooctane, octane, and combinations thereof. The solvent is at least 40% wt. of the total composition. As the composition may be applied to tissue, the solvent is desirably volatile and non-stinging. In one embodiment, at least 60% wt. of the total composition is the solvent. In one embodiment, the composition further comprises an anti-blocking agent. In one embodiment, the viscosity is less than 100 cps.

In one embodiment, the composition further comprises a hemostatic agent, such as a polymerizable cyanoacrylate monomer. Other examples include is hemostatic agents include microfibrillar collagen, chitosan, bone wax, ostene, oxidized cellulose and thrombin.

Cyanoacrylate monomers that may be used include readily polymerizable alpha-cyanoacrylates, including alkyl cyanoacrylates, aryl cyanoacrylates, alkoxyalkyl cyanoacrylates, such as butyl cyanoacrylate and n-butyl cyanoacrylate in particular, octyl cyanoacrylate and 2-octyl cyanoacrylate in particular, ethyl cyanoacrylate, methyl cyanoacrylate, n-dodecyl cyanoacrylate, phenyl 2-cyanoacrylate, methoxyethyl 2-cyanoacrylate, and the like. The composition may be composed of one or more polymerizable cyanoacrylate monomers.

When present, the cyanoacrylate monomer is used in amounts of 1:2 to 2:1, preferably 1.5:1 to 1:1.5 relative to the amount of the copolymer. Generally, the cyanoacrylate is present in at least 5%, by weight, of the nonvolatile portion of the composition, so that the system demonstrates good hemostatic and lymphostatic performance.

If a cyanoacrylate is present, the coating composition desirably an effective amount of a stabilizer (i.e., an amount which provide a coating composition which exhibits substantially no gelation when stored for at least about one month at 22° C., but which, at the same time, is capable of undergoing polymerization at a practical rate). Examples of stabilizers are anionic polymerization inhibitors.

Suitable anionic polymerization inhibitors are well-known to those skilled in the art and include acidic gases such as sulfur dioxide, sulfur trioxide, nitric oxide, and hydrogen fluoride; aromatic sulfonic acids and aliphatic sulfonic acids; and organic sultones of the type disclosed in U.S. Pat. No. 3,836,377 (Delahunty), incorporated herein by reference. Also useful are boric acid or ester chelate or organic acids such as those described in U.S. Pat. No. 4,182,823 (Schoenberg), the silyl esters of sulfonic acids such as those described in U.S. Pat. No. 4,565,883 (Sieger et al.) and the bis-trialkylsilyl esters of sulfuric acid, as described in U.S. Pat. No. 4,650,826 (Waniczek et al.), incorporated herein by reference, and the corresponding silyl esters of phosphoric and phosphonic acid.

Suitable amounts of the foregoing for inclusion in the adhesive base are as follows: a suitable amount of an acidic gas is from about 0.001 to 0.06 parts by weight per 100 parts by weight of the polymerizable monomer; a suitable amount of an aromatic or aliphatic sulfonic acid is from about 0.0005 to 0.1 parts by weight per 100 parts of the cyanoacrylate; and a suitable amount of a sultone is from about 0.1 to 10 parts by weight per 100 parts by weight of the cyanoacrylate.

Typical rheology additives that may be added to the liquid material or formulation are fumed silica, bentonite and other clay derivatives, and the like. Fillers can also be useful in modifying the slip, hardness and blocking performance of the coating. Large particles such as glass beads can be utilized to reduce the blocking performance of the coating.

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety. Examples of suitable colorants as described in U.S. Pat. No. 5,981,621 include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

The use of florescent dyes and pigments are also beneficial by enabling the coating to be viewed under black-light. The coating would be clear and transparent under normal lighting so the site can be easily viewed and inspected for changes in the skin. As a means of ensuring the coating is intact and covering the desired area, the site can be inspected by the use of a backlight wand or flashlight which reveals the coating by its florescence. A particularly useful hydrocarbon soluble fluorescing dye is 2,5-bis(5-tert-butyl-2-benzoxazolyl) 1 thiophene.

Depending on the particular requirements of the user, the compositions can be applied by known means, such as with a spray, pump, swab, rod, sterile brush, sponge applicator or medicine dropper that may be single use or multi use items. The coating compositions are generally sealed prior to application to maintain the stability.

In addition to coating on skin or mucous membranes, the coating composition may be applied to other substrates. Useful substrates may include plastics (e.g., polypropylene, including biaxially oriented polypropylene, vinyl, polyethylene, polyester such as polyethylene terephthalate), nonwovens (e.g., papers, cloths, nonwoven scrims), metal foils, foams (e.g., polyacrylic, polyethylene, polyurethane, neoprene), and the like. In some embodiments, the coating composition may be coated on a low-surface energy substrate so that the resulting coating may be transferred to a second substrate, such as skin. Such low surface energy substrate, known as release materials include materials such as, for example, silicone, polyethylene, polycarbamate, polyacrylics, and the like. It will be understood that the optional cyanoacrylate will limit coating of other substrates.

In some embodiments, island dressings are provided comprises a coating of this disclosure on a backing layer, and an adhesive layer on the backing layer facing the coating. The adhesive layer and backing layer form a perimeter around the instant coating and hold the coating in place on an application surface. A release element is in contact with at least a portion of the edge of the pad proximate the area that the coating and release liner separate during liner removal. Details regarding the construction of such island dressing may be found in US 20110166492 (Burton et al.), incorporated herein by reference.

In one embodiment this disclosure provides a conformable film on an elongatable substrate, wherein the coating weight is from 1 to 30 mg/in$^2$, and wherein the film has less than 75% failure at 100% elongation using the test method described herein. In one embodiment, the film has a thickness of less than 1 mm. In one embodiment, the film fractures less than 75% at 200% elongation. In one embodiment, the film has an elongation of at least 50%. In one embodiment, the film has low tack, drag, and blocking.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Raw materials utilized in the sample preparation are shown in Table 1.

TABLE 1

| Components | | |
|---|---|---|
| Component | Description | Supplier |
| TRIS | 3-[Tris(trimethylsiloxy)silyl]propyl methacrylate | Alfa Aesar (Ward Hill, MA) |
| BA | Behenyl acrylate (Tm = 39° C.)[a], [b] | BASF (Vandalia, IL) |
| t-BMA | tert-Butyl Methacrylate (Tm = −60° C.) | TCI (Portland, OR) |
| SMA | Stearyl Methacrylate (Tm = 20° C.) | TCI (Portland, OR) |
| AA | Acrylic Acid | Alfa Aesar (Ward Hill, MA) |
| Isooctane | 2,2,4-Trimethylpentane | Alfa Aesar (Ward Hill, MA) |
| HMDS | Hexamethyldisiloxane | Alfa Aesar (Ward Hill, MA) |
| Vazo67 | 2,2'-Azobis(2-methylbutyronitrile), | Dupont (Wilmington, DE) |
| Unilin 350 | fully saturated, long aliphatic chain, linear primary alcohols (Tm = 78° C.) | Baker Hughes (Sand Springs, OK) |
| Unilin 425 | fully saturated, long aliphatic chain, linear primary alcohols (Tm = 91° C.) | Baker Hughes (Sand Springs, OK |
| Toluene | Toluene | Alfa Aesar (Ward Hill, MA) |
| OCA | Octyl cyanoacrylate | Cyberbond (Batavia, IL) |
| TsOH | p-Toluenesulfonic acid monohydrate | Alfa Aesar (Ward Hill, MA) |
| Phenolthiazine | Phenolthiazine | Alfa Aesar (Ward Hill, MA) |

[a]Tm = Melting Point
[b] Tm of behenyl acrylate measure by DSC, other Tm as reported from supplier Test Methods
Appearance Solution appearance was assessed in a clear glass vial and rated for clarity. Solutions were rated as either clear, very slight haze (v slt haze), slight haze (slt haze), or hazy.

Viscosity

Viscosity was rated with the solution in a glass vial. The vial was tipped back and forth and the rate of solution flow was rated on a relative scale with low viscosity similar to water rated as 1 and a nonflowing gel rated as 5.

Tack

Several drops of each formulation were spread across a 2.54 cm×5.08 cm CHG gel pad (for example, 3M Tegaderm™ CHG Dressing, catalogue #1657, 3M Company, St. Paul, Minn.). The formulation was spread to a thin film and was allowed to dry for at least 15 minutes at room temperature. Tack is a sensory evaluation conducted by lightly touching the cured coatings with a finger. The coatings were rated from 1 (no tack) to 5 (high tack).

Drag

Several drops of each formulation were spread across a 2.54 cm×5.08 cm CHG gel pad. The formulation was spread to a thin film and was allowed to dry for at least 15 minutes at room temperature. Drag is a sensory evaluation conducted by lightly stroking the cured coatings with a finger. The coatings were rated from 1 (similar frictional force of skin) to 5 (high frictional force).

Blocking

Several drops of each formulation were spread across a 2.54 cm×5.08 cm CHG gel pad. The formulation was spread to a thin film and was allowed to dry for at least 15 minutes at room temperature. Blocking is a sensory evaluation conducted by folding the gel pad over on itself and holding it together with light pressure for 1 minute. The amount of blocking was rated from 1 (no film-film adhesion) to 5 (high, required pulling to separate both sides).

% Failure

Several drops of each formulation were spread across a 2.54 cm×5.08 cm CHG gel pad. The formulation was spread to a thin film and was allowed to dry for at least 15 minutes at room temperature. The CHG gel pads were then stretched to 100% or 200% of their initial length and placed on a flat surface so that they remained in their stretched position. A paper kimwipe (Kimberly Clark, Irving, Tex.) was placed over the stretched surface and several drops of common bleach are placed on top until the entire surface is wet of the coated gel. The kimwipe was removed after 1 minute. If the coating had fractured, the NaOCl in the bleach reacted with the CHG in the gel pad to form a brown color. The amount of brown coloration was reported as a percent failure.

Acrylic Monomers

Acrylic Monomer-1 (AM-1)

To a three-necked 500-mL flask equipped were charged 70.0 g (0.155 mol, based on KOH value) Unilin 350 alcohol, 13.4 g (0.186 mol) AA, 0.5 g p-toluenesulfonic acid monohydrate, 0.06 g phenothiazine, and 130 g toluene. The three-necked flask was equipped with a condenser, Dean Stark trap, air inlet, and mechanical stirrer. The solution was allowed to reflux at 115° C. with stirring. During the reaction, the water byproduct was azeotropically removed from the mixture and collected in the Dean Stark trap. After 4 hours (h), the reaction solution was cooled to room temperature and poured into excess methanol to precipitate the product. The precipitated monomer was filtered with a Buchner funnel under reduced pressure. The filter cake was thoroughly washed with fresh methanol several times and dried at 50° C. in vacuo for 24 h. The melting point for this monomer, as measured by DSC, was 62° C.

Acrylic Monomer 2 (AM-2)

A Unilin 425 based acrylic monomer was synthesized by the procedure described for AM-1, with the following quantities: 70.0 g (0.134 mol, based on KOH value) of Unilin 425 alcohol, 11.59 g (0.160 mol) AA, 0.5 g p-toluenesulfonic acid monohydrate, 0.06 g of phenothiazine, and 130 g toluene. The melting point for this monomer, as measured by DSC, was 66° C.

Octyldecyl acrylate (ODA) Macromer Synthesis

The ODA Macromer may be prepared as described in U.S. Pat. No. 5,604,268, "Examples 20-41", "Hydroxy-terminated Telechelic Polymers". The melting point for this macromer, as measured by DSC, was 50° C.

Copolymer Synthesis

Co-Polymer-1 (P-1)

P-1 was prepared by charging 0.93 g M-1, 1.08 g SMA, 7.44 g t-BMA, 6.3 g TRIS, and 29.25 g isooctane into an amber, pint bottle. The solution was de-aerated with nitrogen purge for 10 minutes at room temperature. Vazo67 (0.3 wt % to total solids) was added to the solution, the bottle capped, placed in water bath at 60° C., and mixed for 24-48 hours. The resulting co-polymer was present at approximately 35-40% solids.

P-2 Through P-60

P2 through P-60 were made as described for P-1, with the monomers and solvents shown in Tables 2 through 5.

TABLE 2

Co-Polymer Formulations

| Co-Polymer | AM-1 (g) | AM-2 (g) | SMA (g) | t-BMA (g) | TRIS (g) | Isooctane (g) |
|---|---|---|---|---|---|---|
| P-1 | 0.93 | 0 | 1.08 | 7.44 | 6.30 | 29.25 |
| P-2 | 0.16 | 0 | 4.86 | 4.44 | 6.30 | 29.25 |
| P-3 | 1.26 | 0 | 4.38 | 3.81 | 6.30 | 29.25 |
| P-4 | 0.16 | 0 | 2.21 | 7.08 | 6.30 | 29.25 |
| P-5 | 0 | 0.93 | 1.08 | 7.44 | 6.30 | 29.25 |
| P-6 | 0 | 0.16 | 4.86 | 4.44 | 6.30 | 29.25 |
| P-7 | 0 | 1.26 | 4.38 | 3.81 | 6.30 | 29.25 |
| P-8 | 0 | 0.16 | 2.21 | 7.08 | 6.30 | 29.25 |

TABLE 3

Co-Polymer Formulations

| Co-Polymer | BA (g) | SMA (g) | t-Butyl MA (g) | TRIS (g) | HMDS (g) |
|---|---|---|---|---|---|
| P-9 | 2.36 | 0.28 | 6.02 | 7.09 | 29.25 |
| P-10 | 4.10 | 0 | 4.58 | 7.09 | 29.25 |
| P-11 | 2.36 | 1.34 | 4.96 | 7.09 | 29.25 |
| P-12 | 4.73 | 0 | 3.94 | 7.09 | 29.25 |
| P-13 | 3.54 | 0.13 | 4.99 | 7.09 | 29.25 |
| P-14 | 2.36 | 0 | 6.79 | 6.60 | 29.25 |
| P-15 | 4.73 | 0 | 7.30 | 3.72 | 29.25 |
| P-16 | 2.36 | 0 | 4.59 | 8.80 | 29.25 |
| P-17 | 4.73 | 0 | 5.11 | 5.92 | 29.25 |
| P-18 | 3.54 | 0 | 5.97 | 6.24 | 29.25 |
| P-19 | 5.99 | 0 | 5.02 | 4.75 | 29.25 |
| P-20 | 5.99 | 0 | 8.10 | 1.66 | 29.25 |
| P-21 | 5.86 | 0 | 6.58 | 3.31 | 29.25 |
| P-22 | 3.56 | 0 | 7.57 | 4.62 | 29.25 |
| P-23 | 4.73 | 0 | 6.95 | 4.08 | 29.25 |

TABLE 4

Co-Polymer Formulations

| Co-Polymer | AA (g) | SMA (g) | TRIS (g) | t-Butyl MA (g) | BA (g) | Isooctane (g) |
|---|---|---|---|---|---|---|
| P-24 | 0.10 | 3.00 | 8.65 | 4.43 | 3.92 | 29.90 |
| P-25 | 0.10 | 0 | 6.64 | 7.36 | 6.00 | 29.90 |
| P-26 | 0.54 | 2.00 | 8.30 | 3.70 | 6.00 | 29.46 |
| P-27 | 0.10 | 0 | 8.60 | 8.34 | 3.06 | 29.90 |
| P-28 | 0.12 | 2.00 | 7.92 | 4.08 | 6.00 | 29.88 |
| P-29 | 0.38 | 0 | 6.43 | 8.97 | 4.61 | 29.62 |
| P-30 | 0.70 | 0 | 8.38 | 8.62 | 3.00 | 29.30 |
| P-31 | 0.69 | 0 | 4.87 | 9.13 | 6.00 | 29.32 |
| P-32 | 0.69 | 3.60 | 8.38 | 4.96 | 3.06 | 29.32 |
| P-33 | 0.37 | 2.00 | 8.25 | 6.75 | 3.00 | 29.63 |
| P-34 | 0.66 | 1.00 | 8.23 | 6.17 | 4.61 | 29.34 |
| P-35 | 0.10 | 0 | 5.47 | 8.53 | 6.00 | 29.90 |
| P-36 | 0.50 | 2.00 | 8.77 | 6.23 | 3.00 | 29.50 |

TABLE 5

Co-Polymer Formulations

| Co-Polymer | AA (g) | AM-1 (g) | AM-2 (g) | ODA Macromer (g) | TRIS (g) | t-Butyl MA (g) | BA (g) | Isooctane (g) |
|---|---|---|---|---|---|---|---|---|
| P-37 | 0.1 | 1.19 | 0 | 0 | 5.24 | 7.87 | 5.60 | 30 |
| P-38 | 0.1 | 0.58 | 0 | 0 | 8.52 | 5.20 | 5.60 | 30 |
| P-39 | 0.1 | 0.40 | 0 | 0 | 12.68 | 1.22 | 5.60 | 30 |
| P-40 | 0.1 | 0.40 | 0 | 0 | 5.18 | 8.72 | 5.60 | 30 |
| P-41 | 0.1 | 1.20 | 0 | 0 | 10.52 | 2.58 | 5.60 | 30 |
| P-42 | 0.1 | 2.00 | 0 | 0 | 3.23 | 9.07 | 5.60 | 30 |
| P-43 | 0.1 | 1.81 | 0 | 0 | 7.02 | 5.47 | 5.60 | 30 |
| P-44 | 0.1 | 2.00 | 0 | 0 | 10.73 | 1.57 | 5.60 | 30 |
| P-45 | 0.1 | 0 | 1.19 | 0 | 5.24 | 7.87 | 5.60 | 30 |
| P-46 | 0.1 | 0 | 0.58 | 0 | 8.52 | 5.20 | 5.60 | 30 |
| P-47 | 0.1 | 0 | 0.40 | 0 | 12.68 | 1.22 | 5.60 | 30 |
| P-48 | 0.1 | 0 | 0.40 | 0 | 5.18 | 8.72 | 5.60 | 30 |
| P-49 | 0.1 | 0 | 1.20 | 0 | 10.52 | 2.58 | 5.60 | 30 |
| P-50 | 0.1 | 0 | 2.00 | 0 | 3.23 | 9.07 | 5.60 | 30 |
| P-51 | 0.1 | 0 | 1.81 | 0 | 7.02 | 5.47 | 5.60 | 30 |
| P-52 | 0.1 | 0 | 2.00 | 0 | 10.73 | 1.57 | 5.60 | 30 |
| P-53 | 0.1 | 0 | 0 | 1.19 | 5.24 | 7.87 | 5.60 | 30 |
| P-54 | 0.1 | 0 | 0 | 0.58 | 8.52 | 5.20 | 5.60 | 30 |
| P-55 | 0.1 | 0 | 0 | 0.40 | 12.68 | 1.22 | 5.60 | 30 |
| P-56 | 0.1 | 0 | 0 | 0.40 | 5.18 | 8.72 | 5.60 | 30 |
| P-57 | 0.1 | 0 | 0 | 1.20 | 10.52 | 2.58 | 5.60 | 30 |
| P-58 | 0.1 | 0 | 0 | 2.00 | 3.23 | 9.07 | 5.60 | 30 |
| P-59 | 0.1 | 0 | 0 | 1.81 | 7.02 | 5.47 | 5.60 | 30 |
| P-60 | 0.1 | 0 | 0 | 2.00 | 10.73 | 1.57 | 5.60 | 30 |

Example Synthesis

Example-1 (E-1)

P-1 was diluted to approximately 30% solids with isooctane. In a glass vial was charged 0.80 g if the diluted P-1 and 1.96 g HMDS. This solution is vortex mixed for 20 seconds or until the solution was homogeneous. If necessary, the solution was heated to 60° C. and vortexed until homogeneous. The solution was then returned to room temperature and 0.24 gms of octyl-cyanoacrylate was added and vortexed until uniform.

E-2 through E-76 were prepared as described in E-1 with the components listed in Tables 6 through 10.

TABLE 6

Example Formulations

| Example | Co-Polymer | Co-Polymer, 30% solids in Isooctane (g) | HMDS (g) | OCA (g) |
|---|---|---|---|---|
| E-1 | P-1 | 0.80 | 1.96 | 0.24 |
| E-2 | P-2 | 0.80 | 1.96 | 0.24 |
| E-3 | P-3 | 0.80 | 1.96 | 0.24 |
| E-4 | P-4 | 0.80 | 1.96 | 0.24 |
| E-5 | P-5 | 0.80 | 1.96 | 0.24 |
| E-6 | P-6 | 0.80 | 1.96 | 0.24 |
| E-7 | P-7 | 0.80 | 1.96 | 0.24 |
| E-8 | P-8 | 0.80 | 1.96 | 0.24 |

TABLE 7

Example Formulations

| Example | Co-Polymer | Co-Polymer, 30% solids in HDMS (g) | HMDS (g) | OCA (g) |
|---|---|---|---|---|
| E-9 | P-9 | 0.80 | 1.96 | 0.24 |
| E-10 | P-10 | 0.80 | 1.96 | 0.24 |
| E-11 | P-11 | 0.80 | 1.96 | 0.24 |
| E-12 | P-12 | 0.80 | 1.96 | 0.24 |
| E-13 | P-13 | 0.80 | 1.96 | 0.24 |
| E-14 | P-14 | 0.80 | 1.96 | 0.24 |
| E-15 | P-15 | 0.80 | 1.96 | 0.24 |
| E-16 | P-16 | 0.80 | 1.96 | 0.24 |
| E-17 | P-17 | 0.80 | 1.96 | 0.24 |
| E-18 | P-18 | 0.80 | 1.96 | 0.24 |
| E-19 | P-19 | 0.80 | 1.96 | 0.24 |
| E-20 | P-20 | 0.80 | 1.96 | 0.24 |
| E-21 | P-21 | 0.80 | 1.96 | 0.24 |
| E-22 | P-22 | 0.80 | 1.96 | 0.24 |
| E-23 | P-23 | 0.80 | 1.96 | 0.24 |

TABLE 8

Example Formulations

| Example | Co-Polymer | Co-Polymer, 30% solids in Isooctane (g) | HMDS (g) | OCA (g) |
|---|---|---|---|---|
| E-24 | P-24 | 0.80 | 1.96 | 0.24 |
| E-25 | P-25 | 0.80 | 1.96 | 0.24 |
| E-26 | P-26 | 0.80 | 1.96 | 0.24 |
| E-27 | P-27 | 0.80 | 1.96 | 0.24 |
| E-28 | P-28 | 0.80 | 1.96 | 0.24 |

TABLE 8-continued

Example Formulations

| Example | Co-Polymer | Co-Polymer, 30% solids in Isooctane (g) | HMDS (g) | OCA (g) |
|---|---|---|---|---|
| E-29 | P-29 | 0.80 | 1.96 | 0.24 |
| E-30 | P-30 | 0.80 | 1.96 | 0.24 |
| E-31 | P-31 | 0.80 | 1.96 | 0.24 |
| E-32 | P-32 | 0.80 | 1.96 | 0.24 |
| E-33 | P-33 | 0.80 | 1.96 | 0.24 |
| E-34 | P-34 | 0.80 | 1.96 | 0.24 |
| E-35 | P-35 | 0.80 | 1.96 | 0.24 |
| E-36 | P-36 | 0.80 | 1.96 | 0.24 |

TABLE 9

Example Formulations

| Example | Co-Polymer (g) | Co-Polymer, 30% solids in HMDS (g) | Co-Polymer, 30% solids in Isooctane (g) | HMDS (g) | OCA (g) |
|---|---|---|---|---|---|
| E-37 | P-37 | 0.8 | 0 | 1.96 | 0.24 |
| E-38 | P-38 | 0.8 | 0 | 1.96 | 0.24 |
| E-39 | P-39 | 0.8 | 0 | 1.96 | 0.24 |
| E-40 | P-40 | 0.8 | 0 | 1.96 | 0.24 |
| E-41 | P-41 | 0.8 | 0 | 1.96 | 0.24 |
| E-42 | P-42 | 0.8 | 0 | 1.96 | 0.24 |
| E-43 | P-43 | 0.8 | 0 | 1.96 | 0.24 |
| E-44 | P-44 | 0.8 | 0 | 1.96 | 0.24 |
| E-45 | P-45 | 0.8 | 0 | 1.96 | 0.24 |
| E-46 | P-46 | 0.8 | 0 | 1.96 | 0.24 |
| E-47 | P-47 | 0.8 | 0 | 1.96 | 0.24 |
| E-48 | P-48 | 0.8 | 0 | 1.96 | 0.24 |
| E-49 | P-49 | 0.8 | 0 | 1.96 | 0.24 |
| E-50 | P-50 | 0.8 | 0 | 1.96 | 0.24 |
| E-51 | P-51 | 0.8 | 0 | 1.96 | 0.24 |
| E-52 | P-52 | 0.8 | 0 | 1.96 | 0.24 |
| E-53 | P-53 | 0 | 0.8 | 1.96 | 0.24 |
| E-54 | P-54 | 0 | 0.8 | 1.96 | 0.24 |
| E-55 | P-55 | 0 | 0.8 | 1.96 | 0.24 |
| E-56 | P-56 | 0 | 0.8 | 1.96 | 0.24 |
| E-57 | P-57 | 0 | 0.8 | 1.96 | 0.24 |
| E-58 | P-58 | 0 | 0.8 | 1.96 | 0.24 |
| E-59 | P-59 | 0 | 0.8 | 1.96 | 0.24 |
| E-60 | P-60 | 0 | 0.8 | 1.96 | 0.24 |

TABLE 10

Example Formulations

| Example | Co-Polymer (g) | Co-Polymer, 30% solids in HMDS (g) | HMDS (g) |
|---|---|---|---|
| E-61 | P-37 | 0.8 | 2.20 |
| E-62 | P-38 | 0.8 | 2.20 |
| E-63 | P-39 | 0.8 | 2.20 |
| E-64 | P-40 | 0.8 | 2.20 |
| E-65 | P-41 | 0.8 | 2.20 |
| E-66 | P-42 | 0.8 | 2.20 |
| E-67 | P-43 | 0.8 | 2.20 |
| E-68 | P-44 | 0.8 | 2.20 |
| E-69 | P-45 | 0.8 | 2.20 |
| E-70 | P-46 | 0.8 | 2.20 |
| E-71 | P-47 | 0.8 | 2.20 |
| E-72 | P-48 | 0.8 | 2.20 |
| E-73 | P-49 | 0.8 | 2.20 |
| E-74 | P-50 | 0.8 | 2.20 |
| E-75 | P-51 | 0.8 | 2.20 |
| E-76 | P-52 | 0.8 | 2.20 |

Results

Test results of the Example formulations are shown in Tables 11 through 15.

TABLE 11

Example Formulation Test Results

| Example | Appearance Before OCA add | Appearance After OCA add | Viscosity [a] | Tack | Blocking | % Failure 100% Elongation | % Failure 200% Elongation |
|---|---|---|---|---|---|---|---|
| E-1 | hazy | hazy | 1 | 1 | 3 | 95 | 98 |
| E-2 | clear | clear | 1 | 4 | 5 | 15 | 90 |
| E-3 | hazy | hazy | 1 | 4 | 5 | 5 | 25 |
| E-4 | v slt haze | v slt haze | 1 | 1 | 2 | 95 | 95 |
| E-5 | hazy | hazy | 1 | 1 | 2 | 90 | 98 |
| E-6 | hazy | hazy | 1 | 3 | 5 | 15 | 35 |
| E-7 | hazy | hazy | 1 | 4 | 5 | 20 | 40 |
| E-8 | slt haze | slt haze | 1 | 1 | 2 | 90 | 98 |

[a] Viscosity evaluated after addition of OCA

TABLE 12

Example Formulation Test Results

| Example | Appearance Before OCA add | Appearance After OCA add | Viscosity [a] | Tack | Drag | Blocking | % Failure 100% Elongation | % Failure 200% Elongation |
|---|---|---|---|---|---|---|---|---|
| E-9 | clear | clear | 1 | 1 | 1 | 1 | 10 | 40 |
| E-10 | clear | clear | 1 | 4 | 1 | 4 | 0 | 15 |
| E-11 | clear | clear | 1 | 1 | 1 | 3 | 2 | 25 |
| E-12 | clear | clear | 1 | 4 | 1 | 5 | 0 | 25 |
| E-13 | clear | clear | 1 | 1 | 1 | 3 | 1 | 40 |
| E-14 | clear | clear | 1 | 1 | 1 | 1 | 45 | 90 |
| E-15 | clear | clear | 1 | 1 | 1 | 1 | 25 | 75 |
| E-16 | clear | clear | 1 | 2 | 1 | 5 | 25 | 75 |
| E-17 | clear | clear | 1 | 3 | 1 | 4 | 10 | 30 |
| E-18 | clear | clear | 1 | 1 | 1 | 2 | 15 | 30 |
| E-19 | v slt haze | slt haze | 1 | 3 | 1 | 4 | 10 | 25 |
| E-20 | hazy | slt haze | 1 | 1 | 1 | 1 | 40 | 55 |
| E-21 | v slt haze | slt haze | 1 | 1 | 1 | 1 | 15 | 60 |
| E-22 | clear | clear | 1 | 1 | 1 | 1 | 60 | 80 |
| E-23 | clear | clear | 1 | 1 | 1 | 1 | 15 | 55 |

[a] Viscosity evaluated after addition of OCA

TABLE 13

Example Formulation Test Results

| Example | Appearance Before OCA add | Appearance After OCA add | Viscosity [a] | Tack | Drag | Blocking | % Failure 100% Elongation | % Failure 200% Elongation |
|---|---|---|---|---|---|---|---|---|
| E-24 | clear | clear | 2 | 2 | 1 | 4 | 10 | 30 |
| E-25 | clear | clear | 2 | 1 | 1 | 1 | 30 | 70 |
| E-26 | clear | clear | 2 | 1 | 1 | 3 | 30 | 45 |
| E-27 | clear | clear | 2 | 1 | 1 | 1 | 98 | 98 |
| E-28 | clear | clear | 2 | 3 | 1 | 4 | 1 | 10 |
| E-29 | clear | clear | 3 | 1 | 1 | 1 | 60 | 85 |
| E-30 | clear | clear | 4 | 1 | 1 | 1 | 65 | 85 |
| E-31 | clear | clear | 3 | 1 | 1 | 1 | 90 | 95 |
| E-32 | clear | clear | 4 | 1 | 1 | 2 | 25 | 80 |
| E-33 | clear | clear | 2 | 1 | 1 | 1 | 45 | 85 |
| E-34 | clear | clear | 2 | 1 | 1 | 1 | 80 | 90 |
| E-35 | clear | clear | 1 | 1 | 1 | 2 | 0 | 5 |
| E-36 | clear | clear | 1 | 1 | 1 | 1 | 1 | 15 |

[a] Viscosity evaluated after addition of OCA

TABLE 14

Example Formulation Test Results

| Example | Appearance Before OCA add | Appearance After OCA add | Viscosity [a] | Tack | Drag | Blocking | % Failure 100% Elongation | % Failure 200% Elongation |
|---|---|---|---|---|---|---|---|---|
| E-37 | hazy | hazy | 1 | 1 | 1 | 1 | 10 | 35 |
| E-38 | hazy | hazy | 1 | 1 | 1 | 2 | 5 | 50 |
| E-39 | hazy | hazy | 1 | 5 | 5 | 5 | 5 | 5 |
| E-40 | hazy | hazy | 1 | 1 | 1 | 1 | 25 | 60 |
| E-41 | hazy | hazy | 1 | 4 | 3 | 5 | 5 | 15 |
| E-42 | hazy | hazy | 1 | 1 | 1 | 1 | 40 | 80 |
| E-43 | hazy | hazy | 1 | 1 | 1 | 3 | 5 | 90 |
| E-44 | hazy | hazy | 1 | 3 | 2 | 4 | 10 | 50 |
| E-45 | hazy | hazy | 1 | 1 | 1 | 1 | 5 | 50 |
| E-46 | hazy | hazy | 1 | 1 | 1 | 5 | 2 | 25 |
| E-47 | hazy | hazy | 1 | 5 | 5 | 5 | 0 | 15 |
| E-48 | hazy | hazy | 1 | 1 | 1 | 1 | 20 | 80 |

TABLE 14-continued

Example Formulation Test Results

| | Appearance | | | | | | % Failure | |
| | Before | After | | | | | | |
| Example | OCA add | OCA add | Viscosity [a] | Tack | Drag | Blocking | 100% Elongation | 200% Elongation |
| --- | --- | --- | --- | --- | --- | --- | --- | --- |
| E-49 | hazy | hazy | 1 | 3 | 4 | 5 | 1 | 10 |
| E-50 | hazy | hazy | 1 | 1 | 1 | 1 | 25 | 95 |
| E-51 | hazy | hazy | 1 | 1 | 1 | 5 | 3 | 80 |
| E-52 | hazy | hazy | 1 | 3 | 3 | 5 | 5 | 75 |
| E-53 | hazy | hazy | 1 | 1 | 1 | 1 | 60 | 98 |
| E-54 | hazy | hazy | 1 | 1 | 1 | 2 | 10 | 95 |
| E-55 | hazy | hazy | 1 | 4 | 3 | 5 | 3 | 40 |
| E-56 | hazy | hazy | 1 | 1 | 1 | 1 | 50 | 98 |
| E-57 | hazy | hazy | 1 | 2 | 2 | 4 | 2 | 60 |
| E-58 | hazy | hazy | 1 | 1 | 1 | 1 | 90 | 98 |
| E-59 | hazy | hazy | 1 | 1 | 1 | 3 | 2 | 35 |
| E-60 | hazy | hazy | 3 | 2 | 2 | 4 | 2 | 45 |

[a] Viscosity evaluated after addition of OCA

TABLE 15

Example Formulation Test Results

| | | | | | | % Failure | |
| Example | Appearance | Viscosity | Tack | Drag | Blocking | 100% Elongation | 200% Elongation |
| --- | --- | --- | --- | --- | --- | --- | --- |
| E-61 | hazy | 1 | 1 | 1 | 2 | 0 | 0 |
| E-62 | hazy | 1 | 2 | 2 | 5 | 0 | 0 |
| E-63 | hazy | 1 | 5 | 5 | 5 | 0 | 0 |
| E-64 | hazy | 1 | 1 | 1 | 1 | 13 | 25 |
| E-65 | hazy | 1 | 5 | 5 | 5 | 0 | 0 |
| E-66 | hazy | 1 | 1 | 1 | 1 | 45 | 55 |
| E-67 | hazy | 1 | 3 | 1 | 5 | 0 | 0 |
| E-68 | hazy | 1 | 5 | 4 | 5 | 0 | 0 |
| E-69 | hazy | 1 | 1 | 1 | 1 | 1 | 15 |
| E-70 | hazy | 1 | 2 | 2 | 5 | 0 | 0 |
| E-71 | hazy | 1 | 5 | 5 | 5 | 0 | 0 |
| E-72 | hazy | 1 | 1 | 1 | 1 | 20 | 50 |
| E-73 | hazy | 1 | 5 | 5 | 5 | 0 | 0 |
| E-74 | hazy | 1 | 1 | 1 | 1 | 20 | 80 |
| E-75 | hazy | 1 | 2 | 1 | 5 | 0 | 1 |
| E-76 | hazy | 1 | 5 | 4 | 5 | 0 | 0 |

This disclosure provides the following embodiments
1. A conformable coating composition comprising:
  a) an acrylate copolymer having a $T_m \geq 30°$ C. comprising at least 5 wt. % of interpolymerized monomer units of monomers having a pendent crystallizable group:
  b) optional cyanoacrylate monomers;
  c) optional cyanoacrylate stabilizer; and
  d) volatile solvent having a solubility parameter from 4.9-12.5 $(cal/cm^3)^{1/2}$.
2. The conformable coating composition of embodiment 1, wherein the copolymer comprises:
  1) 10 to 90 parts by weight of crystalline monomers having a $T_m$ of $\geq 30°$ C.;
  2) 0 to 50 parts by weight of high $T_g$ monomers having a $T_g$ of $\geq 20°$ C.;
  3) 0 to 60 parts by weight silane functional monomers;
  4) 0 to 10 parts by weight of acid functional monomers, based on 100 parts by weight total monomers.
3. The conformable coating composition of any of the previous embodiments wherein the copolymer further comprises 0.5 to 5 parts by weight of acid-functional monomers.
4. The conformable coating of any of the previous embodiments comprising 1 to 50 parts by weight of silane functional monomers.
5. The coating composition of embodiment 4 wherein the silane functional monomer are of the formula:

$A-R^8-[Si-(R^9)_3]_q$, wherein:

A is an ethylenically unsaturated polymerizable group, including vinyl, allyl, vinyloxy, allyloxy, and (meth)acryloyl;

$R^8$ is a covalent bond or a divalent (hetero)hydrocarbyl group, q is at least one;

$R^9$ is a monovalent alkyl, aryl or a trialkylsilyloxy group.
6. The coating composition of embodiment 4 wherein the silane functional monomers are silane macromers.
7. The conformable coating of any of the previous embodiments comprising a high $T_g$ monomer in amounts sufficient that the copolymer has a $T_g$ of $\geq 0°$ C.
8. The coating composition of embodiment 7 comprising 5 to 50 parts by weight of a high $T_g$ monomer.
9. The conformable coating composition of any of the previous embodiments comprising of a cyanoacrylate monomer in a weight ratio of 2:1 to 1:2 relative to the weight of the crystalline copolymer.

10. The conformable coating composition of any of the previous embodiments further comprising a cyanoacrylate stabilizer.

11. The conformable coating composition of any of the previous embodiments comprising at least 40 wt. % of solvent relative to a), b) and c).

12. The conformable coating composition of embodiment 11 wherein the solvent is a siloxane solvent.

13. The conformable coating composition of any of the previous embodiments wherein the copolymer has a $T_g$ of >0° C.

14. The conformable coating composition of any of the previous embodiments wherein the copolymer has a crystalline melting point of ≥20° C. range as measured by DSC.

15. The conformable coating composition of any of the previous embodiments, wherein the copolymer has a molecular weight, $M_w$, from 100,000 to 5,000,000.

16. The composition of any of the previous embodiments wherein the crystallizable monomers having a $T_m$ of ≥30° C. are selected from:
   a) (meth)acrylate ester monomers of linear, primary alkanols;
   b) secondary alcohols or singly branched primary alkanols of at least 24 carbon atoms;
   c) linear alkenyl esters of at least 24 carbon atoms;
   d) aralkyl or aralkenyl esters of having a linear alkyl of at least 24 carbon atoms; or
   e) crystalline macromers of (meth)acrylate ester monomers having a pendent alkyl group of at least 16 carbon atoms.

17. The coating composition of any of the previous embodiments where the crystalline monomers are of the formula:

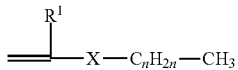

where
R is hydrogen or a ($C_1$-$C_4$) alkyl group,
X is —$CH_2$—, —C(O)O—, —O—C(O)—, —C(O)—NH—, —HN—C(O)—, —O—, —NH—, O—C(O)—NH—, —HN—C(O)—O, —HN—C(O)—NH—, or —Si($CH_3$)$_2$—, and
n is sufficient to impart at least one distinct crystalline melting point≥30° C.

18. The coating composition of embodiment 17 where n is at least 18.

19. The coating composition of any of the previous embodiments comprising a crystalline copolymer of the formula: crystalline copolymer may be represented by the general formula:

~[$M^{xstal}$]$_v$-[$M^{silane}$]$_w$-[$M^{acid}$]$_x$-[$M^{highTg}$]$_y$~, wherein v is 10 to 90 parts by weight of crystalline monomers having a $T_m$ of ≥30° C.;
w is 0 to 60 parts by weight silane functional monomers;
x is 0 to 10 parts by weight of acid functional monomers,
y is 0 to 50 parts by weight of high $T_g$ monomers having a $T_g$ of ≥20° C.

20. A conformable film comprising the dried coating composition of embodiments 1-19.

21. The conformable film of embodiment 20 wherein the film has less than 75% failure at 100% elongation.

22. A multilayer article comprising a layer of the conformable film of any of embodiments 19-21 on a substrate.

The invention claimed is:

1. A conformable coating composition comprising:
   a) an acrylate copolymer having a $T_m$≥30° C. derived from interpolymerized crystalline monomer units of monomers having a pendent crystallizable group:
   b) optional cyanoacrylate monomers;
   c) optional cyanoacrylate stabilizer; and
   d) volatile solvent having a solubility parameter from 4.9-12.5 $(cal/cm^3)^{1/2}$; wherein the copolymer is derived from:
1) 10 to 90 parts by weight of crystalline monomers having a $T_m$ of ≥30° C. selected from:
   a) (meth)acrylate ester monomers of linear, primary alkanols of at least 20 carbon atoms;
   b) (meth)acrylate ester monomers of secondary alcohols or singly branched primary alkanols of at least 24 carbon atoms;
   c) linear alkenyl esters of at least 24 carbon atoms;
   d) aralkyl or aralkenyl esters of having a linear alkyl of at least 24 carbon atoms; or
   e) crystalline macromers of (meth)acrylate ester monomers having a pendent alkyl group of at least 16 carbon atoms;
2) 0 to 50 parts by weight of high $T_g$ monomers having a $T_g$ of ≥20° C.;
3) 0 to 60 parts by weight silane functional monomers;
4) 0 to 10 parts by weight of acid functional monomers, based on 100 parts by weight total monomers;
   wherein the dried coating composition has less than 75% failure at 100% elongation.

2. The conformable coating composition of claim 1 wherein the copolymer is further derived from 0.5 to 5 parts by weight of acid-functional monomers.

3. The conformable coating of claim 1 wherein the copolymer is derived from 1 to 50 parts by weight of silane functional monomers.

4. The coating composition of claim 3 wherein the silane functional monomer are of the formula:

A-$R^8$-[Si—($R^9$)$_3$]$_q$, wherein:

A is an ethylenically unsaturated polymerizable group, including vinyl, allyl, vinyloxy, allyloxy, and (meth)acryloyl;
$R^8$ is a covalent bond or a divalent (hetero)hydrocarbyl group, q is at least one;
$R^9$ is a monovalent alkyl, aryl or a trialkylsilyloxy group.

5. The coating composition of claim 1 wherein the silane functional monomers are siloxane macromers.

6. The conformable coating of claim 1 wherein the copolymer is derived from a high $T_g$ monomer in amounts sufficient that the copolymer has a $T_g$ of ≥0° C.

7. The conformable coating of claim 6 wherein the copolymer is derived from 5 to 50 parts by weight of a high $T_g$ monomer.

8. The conformable coating composition of claim 1 comprising of a cyanoacrylate monomer in a weight ratio of 2:1 to 1:2 relative to the weight of the crystalline copolymer.

9. The conformable coating composition of claim 8 further comprising a cyanoacrylate stabilizer.

10. The conformable coating composition of claim 1 comprising at least 40 wt. % of solvent relative to a), b) and c).

11. The conformable coating composition of claim 1 wherein the solvent is a siloxane solvent.

12. The conformable coating composition of claim 1, wherein the copolymer has a molecular weight, $M_w$, from 100,000 to 5,000,000.

13. The coating composition of claim 1 comprising a crystalline copolymer of the formula:

$$\sim[M^{xstal}]_v\text{-}[M^{silane}]_w\text{-}[M^{acid}]_x\text{-}[M^{highTg}]_y\sim, \text{ wherein}$$

v is 10 to 90 parts by weight of crystalline monomers having a $T_m$ of $\geq 30°$ C.;

w is 0 to 60 parts by weight silane functional monomers;

x is 0 to 10 parts by weight of acid functional monomers, y is 0 to 50 parts by weight of high $T_g$ monomers having a $T_g$ of $\geq 20°$ C.

14. A multilayer article comprising a layer of the conformable film coating composition of claim 13 on a substrate.

* * * * *

UNITED STATES PATENT AND TRADEMARK OFFICE
CERTIFICATE OF CORRECTION

PATENT NO. : 9,962,461 B2  
APPLICATION NO. : 15/124132  
DATED : May 8, 2018  
INVENTOR(S) : Robert Asmus Page 1 of 1

It is certified that error appears in the above-identified patent and that said Letters Patent is hereby corrected as shown below:

In the Specification

Column 8,
Line 18, delete "$(cal/cm)^{1/2}$." and insert -- $(cal/cm^3)^{1/2}$. --, therefor.

Signed and Sealed this
Thirty-first Day of July, 2018

Andrei Iancu
*Director of the United States Patent and Trademark Office*